United States Patent
Schmotzer

(12) 
(10) Patent No.: US 6,258,127 B1
(45) Date of Patent: Jul. 10, 2001

(54) TIBIA PART OF A NEW JOINT ENDOPROSTHESIS

(75) Inventor: Hans Schmotzer, Aarau (CH)

(73) Assignee: PLUS Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/254,853

(22) PCT Filed: Sep. 11, 1997

(86) PCT No.: PCT/EP97/04981

§ 371 Date: Jul. 23, 1999

§ 102(e) Date: Jul. 23, 1999

(87) PCT Pub. No.: WO98/10721

PCT Pub. Date: Mar. 19, 1998

(30) Foreign Application Priority Data

Sep. 11, 1996 (DE) .............................................. 196 36 935
Oct. 2, 1996 (DE) .............................................. 196 40 798

(51) Int. Cl.[7] ...................................................... A61F 2/38
(52) U.S. Cl. .................................. 623/20.32; 623/20.14; 623/20.34; 623/20.33
(58) Field of Search ................................. 623/20, 16, 18, 623/19, 23, 22, 20.14, 20.15, 20.16, 20.21, 20.22, 20.23, 20.27, 20.32, 20.33, 20.34

(56) References Cited

U.S. PATENT DOCUMENTS

| | | | |
|---|---|---|---|
| 4,213,209 | * | 7/1980 | Insall et al. ............................. 623/20 |
| 4,822,362 | * | 4/1989 | Walker et al. .......................... 623/20 |
| 4,892,547 | * | 1/1990 | Brown .................................... 623/20 |
| 4,938,769 | * | 7/1990 | Shaw ...................................... 623/20 |
| 5,137,536 | * | 8/1992 | Koshino ................................. 623/20 |
| 5,176,711 | | 1/1993 | Grimes . |
| 5,192,329 | | 3/1993 | Christie et al. . |
| 5,201,768 | | 4/1993 | Caspari et al. . |
| 5,326,368 | | 7/1994 | Collazo . |
| 5,413,604 | * | 5/1995 | Hodge .................................... 623/20 |
| 5,571,198 | | 11/1996 | Drucker et al. . |

FOREIGN PATENT DOCUMENTS

| | | | |
|---|---|---|---|
| 28 02 655 | | 8/1978 | (DE) . |
| 32 05 526 | | 9/1983 | (DE) . |
| 42 11 347 | | 10/1993 | (DE) . |
| 42 301 18 | | 3/1994 | (DE) . |
| 43 37 936 | | 5/1995 | (DE) . |
| 0 303 006 | | 2/1989 | (EP) . |
| 0 380 045 | | 8/1990 | (EP) . |
| 384854 | | 8/1990 | (EP) . |
| 0 551 791 | | 7/1993 | (EP) . |
| 0 552 949 | | 7/1993 | (EP) . |
| 0 612 509 | | 8/1994 | (EP) . |
| 611 559 | | 8/1994 | (EP) . |
| 0 709 075 | | 5/1996 | (EP) . |
| 2700263 | * | 1/1994 | (FR) ....................................... 623/20 |
| 2 715 556 | | 8/1995 | (FR) . |
| WO 92/15261 | | 9/1992 | (WO) . |
| 95/24874 | | 9/1995 | (WO) . |

* cited by examiner

*Primary Examiner*—Pedro Philogene
(74) *Attorney, Agent, or Firm*—Knobbe, Martens, Olson & Bear, LLP

(57) ABSTRACT

A tibia part of a knee joint prosthesis includes a tibia platform having a distal side, and an anchoring element. The anchoring element is arranged on the distal side of the tibia platform and attached to the tibia platform. In one embodiment, the anchoring element is formed by a shield having a height which is smaller than a width of the shield, and the shield has a U-, C- or V-shape as seen from the tibia platform.

19 Claims, 3 Drawing Sheets

TIBIA PART OF A NEW JOINT ENDOPROSTHESIS

FIELD OF THE INVENTION

The invention relates to a tibia part of a new joint endoprosthesis with a tibia platform or tibia plateau and with an anchoring element which is arranged on the distal side of the tibia platform and which may be screwed to the tibia platform.

BACKGROUND OF THE INVENTION

In a cement free knee joint replacement, additional stabilisation of a tibia platform by means of Spongiosa screws is the state of the art. In addition to the screws, often pegs, webs or ribs which are connected to the plateau, are common. The advantage of screws lies in the fact that, as a result of the initial stress produced thereby, a compression force is produced between the tibia platform and the bone during implantation. As a result, the primary stability is increased. Furthermore, bone is encouraged to grow into the distal or rear surface of the tibia platform. However, anchoring with screws has the disadvantage that the latter can be displaced backwards if osteonecroses or osteolyses occur under the tibia platform. Furthermore, the danger exists in the previously mentioned construction that detached polyethylene particles which originate from the polyethylene inlay mounted on the proximal side are displaced through the screw holes formed in the tibia platform into the bone. This then leads to local osteolyses.

In the relevant literature, there are described various cylindrical expansion anchors on the distal side of the tibia platform. These have the advantage that they make a pretension force possible. However, since they are based on the expansion principle there is no assurance that the anchor remains securely connected to the tibia platform. The possibility exists of being displaced and hence the formation of a gap between expansion anchor and tibia plateau. Polyethylene particles, coming from the mentioned inlay, may be displaced through this gap into the bone and lead to osteolyses. In addition, the point shaped support which is produced by anchors is disadvantageous for a long term osteointegration of the implant.

As an alternative to short anchors, a long intramedullar support can be used. This support can be completed by ribs by means of which a somewhat more widespread supporting of the tibia platform is obtained. A construction of this type is known e.g. from U.S. Pat. No. 4,938,769. The use of an intramedullar support has the disadvantage however that the load transference takes place in the distal region. The proximal bone beneath the tibia platform is in contrast only slightly stressed. This effect, so called "stress shielding" leads to bone resorption and in the long term to loosening of the implant.

SUMMARY OF THE INVENTION

It would therefore be of advantage if by means of an appropriate construction, on the one hand pre-tension could be produced during implantation and if simultaneously the tibia platform and the anchoring element formed a unit so that, in the first place, displacing of the anchoring element is impossible and secondly a hermetic seal occurs against the detached polyethylene particles.

An aspect of the invention involves a tibia part of a knee joint prosthesis. The tibia part comprises anchoring element and a tibia platform which has a distal side. The anchoring element is arranged on the distal side of the tibia platform and attached to the tibia platform. Correspondingly, the anchoring element according to the invention is formed by a shield in the form of a U-, C- or V- shape as seen from the front, the height of which is smaller than the width. It is therefore crucial that the anchoring shield in its implanted condition has a greater horizontal extension than vertical extension or rather height. As a result of the relatively small height of the anchoring shield the occurrence of distal load transference is prevented. At the same time, the large-surface support in the bone offers increased resistance to horizontal transverse loads and hence tilting of the tibia platform. In order to produce a pre-stressing force during implantation, the anchoring shield is firstly inserted into the proximal tibia bone and indeed so far that the upper edge of the anchoring shield is sunk to a slight extent beneath the bone surface. Next, the tibia platform is screwed into the anchoring shield which is sunk in the bone. As a consequence, a pre-stress force between the tibia platform and the bone is produced because of the friction between the anchoring shield and the bone. Since no expansion effect occurs, the shield can adjust in a proximal direction and hence be screwed to the tibia platform to be flush and free from play without the pre-stress force being noticeably lost.

The distal edge of the anchoring shield is arc-shaped, in particular formed to be convexly arc shaped, the arc line defining an arc of a circular section, elliptical section or a parabola. By means of this configuration, the anchoring shield can be inserted more easily into the proximal tibia bone. In addition, it should be pointed out that to avoid a loss of a pre-stress force the wall surfaces of the anchoring shield extend parallel to one another. In one embodiment, thickness or wall strength of the anchoring shield decreases step wise from proximal to distal.

In order to achieve an even better anchoring in the proximal tibia bone, the anchoring shield embraces, according to a further embodiment, a central web which is in the region of maximal height or at approximately half the width and which extends in the manner of a bisector of the lateral and medial portions of the anchoring shield. If required a further anchoring web can be arranged diametrally thereto. However, it has been shown that as a rule the previously mentioned central web is adequate for difficult anchoring cases. This central web extends preferably over the entire height of the anchoring shield. However, it is also conceivable to design the central web to be somewhat shorter than the corresponding height of the anchoring shield.

In order to secure the anchoring shield to the distal side of the tibia platform, the anchoring shield has at least two especially three proximally accessible threaded borings into which screws extending through corresponding borings in the tibia platform may be screwed for securing the tibia platform to the anchoring shield. The threaded borings are preferably arranged centrally and at the lateral and also medial end of the anchoring shield. For this purpose, the anchoring shield is designed peg-like at the assigned spots respectively.

For easier inserting of the anchoring shield into the tibia bone, the distal edge of the anchoring shield is designed as a cutting edge.

A further embodiment is distinguished in that on the distal side of the tibia platform a grooved shape recess is incorporated into which the anchoring shield may be fitted by its proximal front side securely.

In order to increase the pre-stress force of the anchoring shield in the tibia bone, the surface of same is preferably roughened, especially structured and indeed structured in a longitudinal direction. As a consequence, the pre-stress force is also not lost if the anchoring shield is displaced in a proximal direction when screwing down the tibia platform. The enlargement of the contact surface between the anchoring shield and the tibia bone is crucial.

BRIEF DESCRIPTION OF THE DRAWINGS

Preferred embodiments of a tibia part which is constructed according to the invention are explained subsequently in greater detail with reference to the enclosed drawings which show.

DETAILED DESCRIPTION OF THE INVENTION

Figure 1:
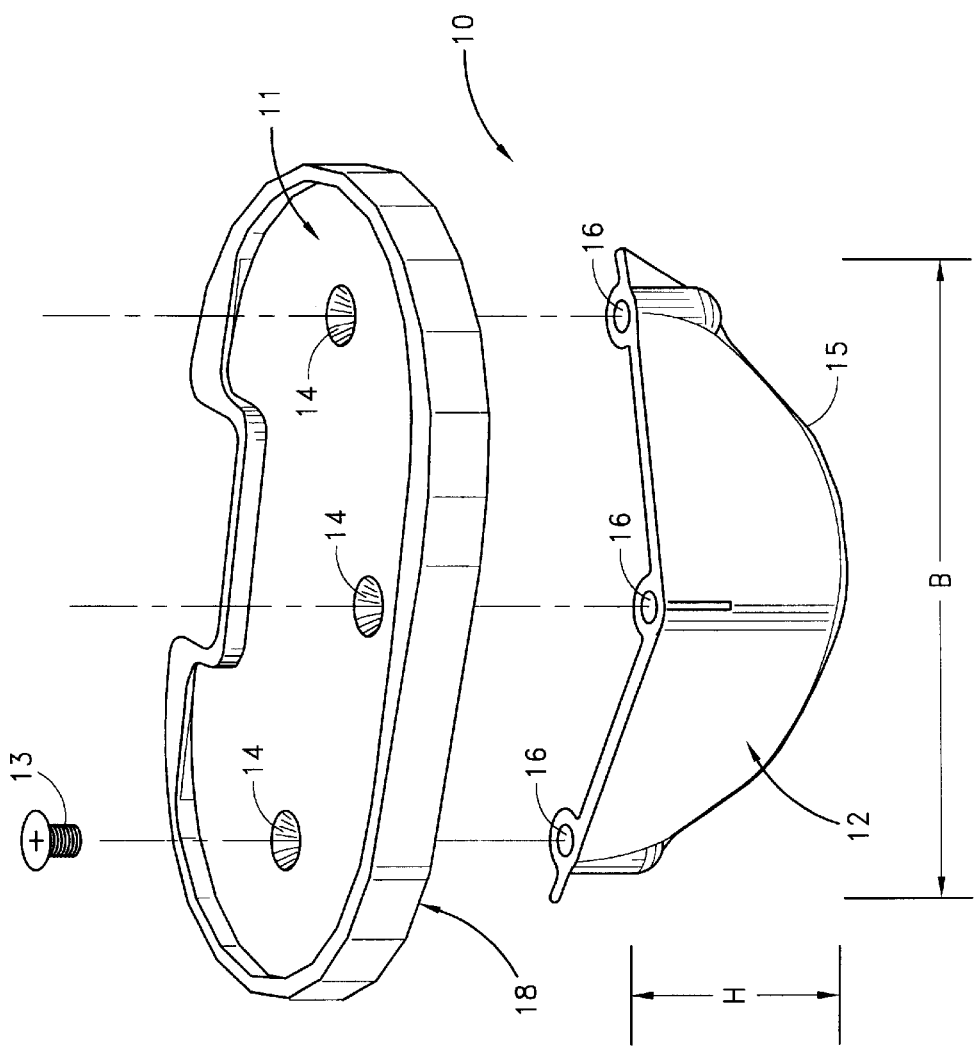
FIG. 1: a first embodiment of a tibia part according to the invention in perspective exploded representation.

The tibia part shown in FIG. 1 is characterised with the reference number 10 which is placed above. It comprises a tibia platform or a tibia plateau 11 and an anchoring element arranged on the distal side in the form of an anchoring shield 12. The anchoring shield is angled in a V-shaped in front view. The height "H" is noticeably smaller than the width "B" in the shown embodiment, the height "H" of the anchoring shield 12 is roughly half the projected width "B". Instead of the V-shaped angle the anchoring shield 12 can also be formed U- or C-shaped in front view.

The anchoring shield 12 is screwed to the tibia platform 11 by means of screws 13 which extend through borings 14 in the tibia platform 11 in such a manner that the proximal front side of the anchoring shield abuts the distal side of the tibia platform along the full surface.

The distal edge 15 of the anchoring shield 12 is configured arc shaped, namely convexly arc shaped. The arc line can define an arc section, an elliptical section or a parabola.

For the purpose of screwing down the anchoring shield 12 and the tibia platform 11, the anchoring shield 12 has three proximally accessible threaded borings 16 into which the screws 13 extending through corresponding borings 14 in the tibia platform 11 may be screwed for securing the tibia platform 11 to the anchoring shield 12. The screws 13 are oval headed screws or flat headed screws.

The threaded borings 16 are central in the shown embodiment, given by way of example, i.e. arranged or constructed in the region of the angle of anchoring shield and at the lateral and also at the medial ends of the same. For this purpose, the anchoring shield is designed thickened at these points and roughly peg-shaped. The distal edge 15 of the anchoring shield 12 may even be designed preferably as a cutting edge.

The surface of the anchoring shield is roughened, especially longitudinally structured. In the embodiment according to FIG. 3, which is described in even more detail further down, the surface structuring can also extend transversely since, in this embodiment, the anchoring shield remains immovable after being inserted into the tibia bone. The anchoring shield also is not displaced in a proximal direction during securing of the tibia platform.

Figure 2:
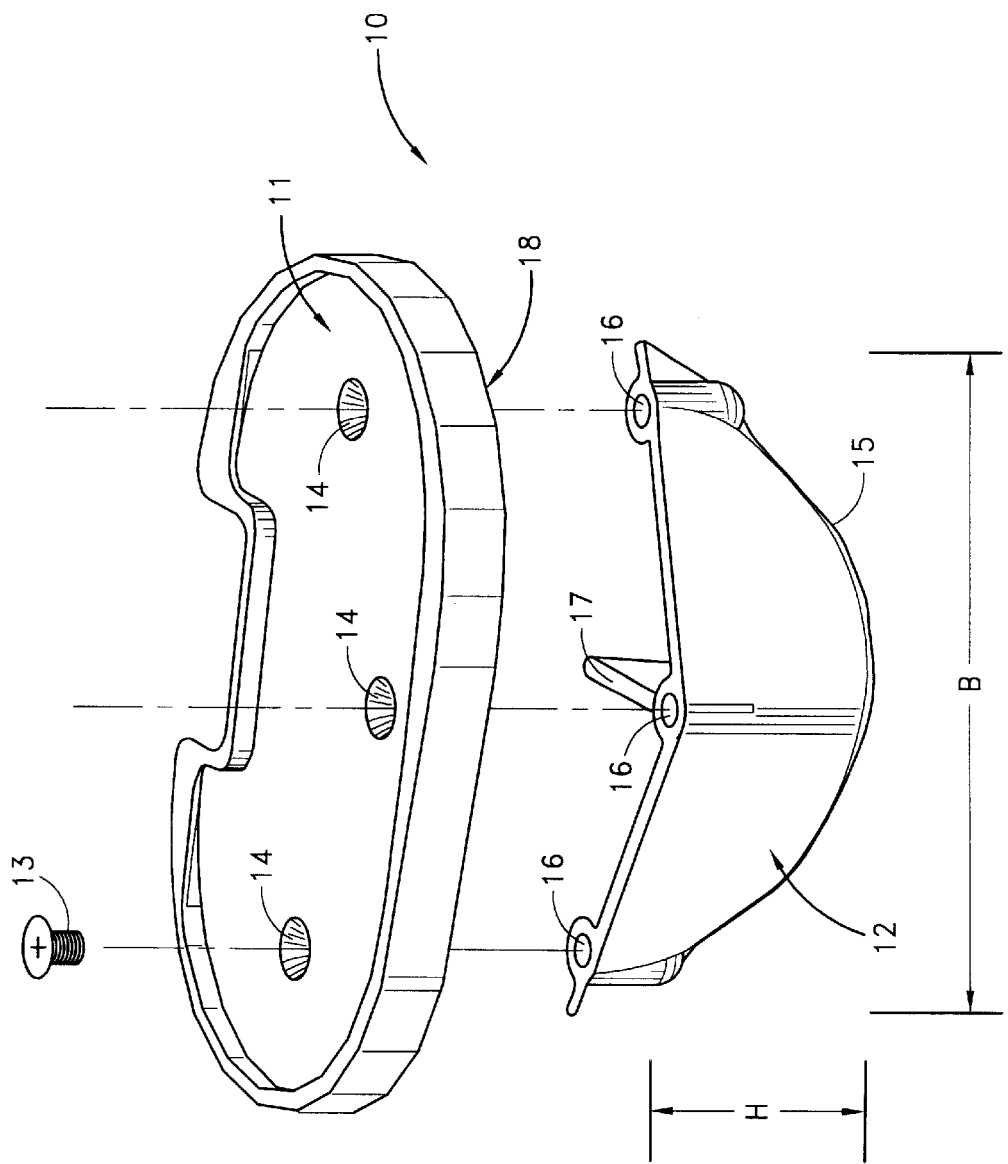
FIG. 2: a second embodiment of a tibia part according to the invention in perspective exploded representation.

The embodiment according to FIG. 2 differs from the one according to FIG. 1 in that in the region of maximal height or at roughly half the width the anchoring structure encompasses a central web 17 which extends in the manner of a bisector between the lateral and medial section of the anchoring shield 12. Moreover this embodiment corresponds to the one according to FIG. 1 so that a further description of same is superfluous. The central web 17 is therefore arranged centrally and directed in a dorsal direction in its implanted state. Said web 17 offers additional support for the tibia platform. The posterior backwards displacement of the tibia platform is reduced, if the resulting joint force is displaced dorsally as occurs while bending. Furthermore, it may also be mentioned about the embodiment according to FIG. 2 that the peg-like thickenings for forming the threaded borings 16 form the lateral and medial closure of the anchoring shield 12. The middle or central web 17 may likewise be provided at the ends with such a peg-like thickening for forming a threaded boring.

Figure 3:
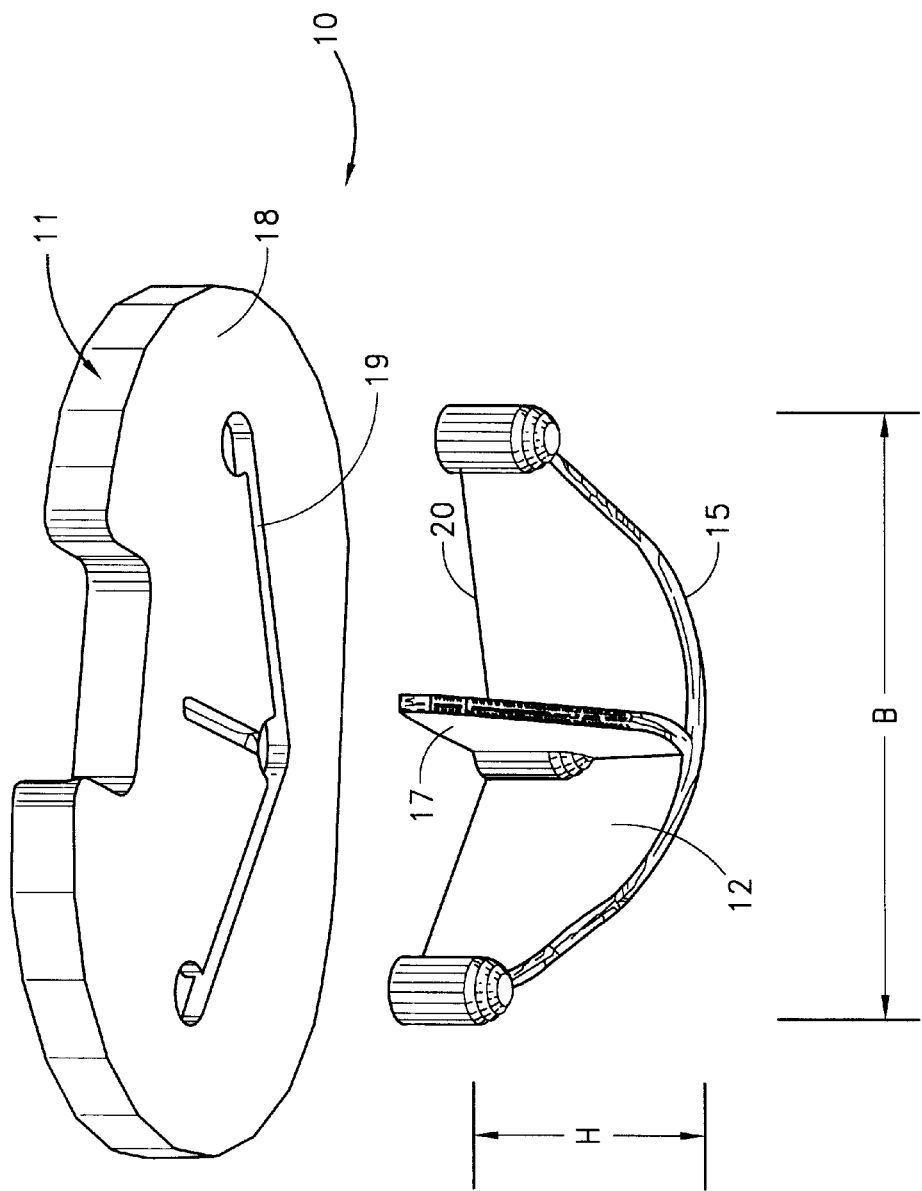
FIG. 3: a further embodiment of a tibia part according to the invention in perspective exploded representation.

The central web 17 extends preferably over the entire height "H" of the anchoring shield 12, as can be seen in the embodiment according to FIG. 3. However, it is also conceivable to construct the height of the central web 17 to be somewhat reduced.

The embodiment according to FIG. 3 differs from the embodiment according to FIGS. 1 and 2 in that on the distal side 18 of the tibia platform 11 a groove shaped recess 19 is incorporated into which the anchoring shield 12 can be fitted by its proximal front side 20 in a play- free manner. The geometry of the groove-like recess 19 corresponds of course to the geometry of the front side 20 of the anchoring shield 12. This embodiment has the advantage that the anchoring shield does not require to be inserted into the tibia bone in a recessed manner since the gap required for bracing is already incorporated in the tibia platform. The further advantage exists that the seal between the tibia platform and the anchoring shield is improved.

The outer edge of the central web 17 is directed towards the anchoring shield 12 in a proximal to distal direction. As a result, the inserting of the anchoring shield 12 into the tibia bone is facilitated.

The proximal side of the tibia platform 11 is designed in the conventional manner to receive a polyethylene inlay.

The described tibia part consists of a bio-compatible material, especially titanium or titanium alloy as is normal for endoprosthetics.

The two part design of the described tibia part is comparatively simple as far as production technique is concerned. Hence, in DE 30 13 155 C2 for example a one-piece embodiment is shown and described. This is exceedingly demanding from a production technique point of view. Complicated shapes are required. Reprocessing is also only possible at a high cost. Furthermore, this known embodiment has the disadvantages portrayed above with reference to U.S. Pat. No. 4,938,769 of so-called stress shielding.

It may also be pointed out that the distal edge 15, in the embodiment according to FIGS. 2 and 3, between the central web 17 and the lateral or medial end of the anchoring shield 12 respectively can extend in a straight line or arc concavely.

It might also be mentioned that the distal or lower side 18 of the tibia platform 11 is preferably provided with projections which are arranged at a spacing from one another. The projections can have the form of ribs, cutting edges, pegs, cylinders, needles or similar. By means of projections of this type, growth of the bone onto the platform 11 is encouraged.

Tests have shown that a mutual spacing of the mentioned projections in the order of 3 to 6 mm, especially 4 to 5 mm is particularly advantageous for growing of the bone. The height of the projections is roughly 0.5 to 2.5 mm, especially approximately 1 mm.

It might also be mentioned finally, that it is advantageous to provide the surface of the anchoring shield with a transverse structure, especially in the form of transverse ribs or transverse teeth. As a consequence, the hold of the anchoring shield 12 on the bone can be increased without the connection of the shield to the tibia platform being impeded.

The mentioned transverse structuring leads to a type of interlocking of the anchoring shield to the bone. As long as a longitudinal structure is provided, the anchoring in the bone is consequently likewise increased, indeed because of the enlarged contact surface between the anchoring shield and the bone.

The entirety of features present in the application documents are claimed to be essential to the invention insofar as they, on an individual basis or in combination, are new relative to the state of the art.

List of Reference Numbers:

10 tibia part
11 tibia platform
12 anchoring shield
13 screws
14 boring
15 distal edge
16 threaded boring
17 central web
18 distal side
19 groove-shaped recess
20 proximal front side

What is claimed is:

1. A tibia part of a knee joint prosthesis, comprising:
   a tibia platform having a distal side; and
   an anchoring element arranged on the distal side of the tibia platform and attached to the tibia platform, the anchoring element formed by a shield having a height which is smaller than a width of the shield, the shield having an upper surface facing the distal side of the tibia platform, a shape selected from a group consisting of a U-shape, C-shape and V-shape, and a distal edge which is convexly arc-shaped, an arc line of the distal edge defining a section selected from the group consisting of a circular section, an elliptical section, and a parabola.

2. The tibia part of claim 1, further comprising a central web positioned in an area in which the height of the shield is maximal, the central web bisecting the shield into a lateral portion and a medial portion.

3. The tibia part of claim 2, wherein the central web extends over the entire height of the shield.

4. The tibia part of claim 1, wherein the shield has at least two proximally accessible threaded borings at the upper surface, the threaded borings receiving screws extending through corresponding borings in the tibia platform to secure the tibia platform to the shield.

5. The tibia part of claim 4, wherein the shield has three threaded borings.

6. The tibia part of claim 4, wherein the threaded borings are placed centrally on the lateral portion and the medial portion of the anchoring shield.

7. The tibia part of claim 1, wherein a distal edge of the shield is designed as a cutting edge.

8. The tibia part of claim 1, wherein the anchoring shield is connected to the distal side of the tibia platform along the upper surface and without play.

9. The tibia part of claim 1, further comprising a recess on the distal side of the tibia platform, the recess configured to receive a proximal front side of the shield without play.

10. The tibia part of claim 1, wherein a shield surface is roughened or structured.

11. The tibia part of claim 1, wherein the distal side of the tibia platform comprises projections which are arranged at a spacing from one another sufficient to encourage growth of bone onto the tibia platform.

12. The tibia part of claim 11, wherein the projections have a shape selected from a group consisting of ribs, cutting edges, pegs, needles, and cylinders.

13. The tibia part of claim 11, wherein the projections on the distal side of the tibia platform have a spacing of approximately 3–6 mm.

14. The tibia part of claim 11, wherein the projections have a spacing of approximately 4–5 mm.

15. The tibia part of claim 10, wherein the shield surface has a structure that has at least one of a longitudinal and transverse orientation.

16. The tibia part of claim 15, wherein the shield surface comprises teeth which have at least one of a longitudinal and transverse orientation.

17. A tibia part of a knee joint prosthesis, comprising:
   a tibia platform having a distal side; and
   an anchoring element arranged on the distal side of the tibia platform and attached to the tibia platform, the anchoring element formed by a shield having a height which is smaller than a width of the shield, the shield having a proximal edge facing the distal side of the tibia platform, said shield having a distal edge configured for insertion into bone, wherein said shield decreases in thickness in a stepwise manner from said proximal edge to said distal edge such that opposing wall surfaces of the shield remain parallel at each step.

18. A method of installing a knee joint prosthesis, said prosthesis comprising a tibia platform and an anchoring element, said method comprising:
   inserting said anchoring element into a proximal portion of a tibia bone until an upper surface of said anchoring element is sunk beneath the tibia bone surface; and
   securing said tibia part to said anchoring element.

19. The method of claim 18, wherein said anchoring element comprises a shield having a height which is less than a width of said shield.

* * * * *